US00PP27202P2

(12) United States Plant Patent
Van Swieten

(10) Patent No.: US PP27,202 P2
(45) Date of Patent: Sep. 27, 2016

(54) ***PHALAENOPSIS* ORCHID PLANT NAMED 'PHALFOLAK'**

(50) Latin Name: ***Phalaenopsis* hybrid**
Varietal Denomination: PHALFOLAK

(71) Applicant: ANTHURA B.V., Bleiswijk (NL)

(72) Inventor: Martinus Nicolaas Gerardus Van Swieten, Leimuiden (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 14/545,766

(22) Filed: Jun. 16, 2015

(51) Int. Cl.
*A01H 5/02* (2006.01)

(52) U.S. Cl.
USPC ..... Plt./311

(58) Field of Classification Search
USPC ..... Plt./311
CPC ..... A01H 5/02
See application file for complete search history.

*Primary Examiner* — Kent L Bell
(74) *Attorney, Agent, or Firm* — Jondle & Associates, P.C.

(57) ABSTRACT

A new and distinct variety of *Phalaenopsis* plant named 'PHALFOLAK', particularly characterized by having yellow striped flowers, 1 to 3 peduncles, a peduncle that is short and sturdy, leaves that are lanceolate and moderately elongated, and is propagated by tissue culture is disclosed.

3 Drawing Sheets

Genus and species: *Phalaenopsis* hybrid.
Variety denomination: 'PHALFOLAK'.

BACKGROUND OF THE NEW PLANT

The present invention comprises a new and distinct cultivar of *Phalaenopsis* plant, botanically known as *Phalaenopsis* of the Orchidaceae family, and hereinafter referred to by the cultivar name 'PHALFOLAK'.

*Phalaenopsis* comprises a genus of about 60 species of herbaceous perennials many of which, or the hybrids thereof, are suitable for cultivar in the home or greenhouse. *Phalaenopsis* is predominantly epiphytic or rock dwelling, and is native to tropical Asia, the Malay Archipelago, and Oceania. The species typically has 2-ranked, fleshy, oblong or elliptic leaves affixed to a short central stem (monopodial growth), which vary in size from 12 to 20 cm to over 60 cm. The leaves may be entirely green or mottled with silver grey.

*Phalaenopsis* orchids, often referred to as 'Moth Orchids' in the horticultural trade, are frequently used to furnish cut flowers for the florist trade or sold as flowering potted-plants for home or interiorscape.

*Phalaenopsis* produces upright or pendent lateral racemes or panicles, often with many showy flowers which open in succession beginning with the lowermost. The flowers possess three sepals and three petals; the lateral ones being alike. The lowermost petals, called the labellum, are three-lobed and are often more brightly-colored than the other flower segments. Flower colors include various shades of pink, white, yellow, and red-brown.

*Phalaenopsis* orchids are typically propagated from seeds. Asexual propagation of *Phalaenopsis* is often done from off-shoots which arise from the lower bracts of the inflorescence. The resulting plants are detached from the mother plants and may be planted in a suitable substrate.

The new *Phalaenopsis* 'PHALFOLAK' is particularly characterized by its attractive and unique yellow striped flowers, economical propagation by tissue culture, rapid growth, and a plant dimension suitable for packaging and shipping to the market.

'PHALFOLAK' is a product of a planned breeding program conducted by the inventor in Bleiswijk, The Netherlands.

The new *Phalaenopsis* 'PHALFOLAK' originated from a cross made in July 2007 in Bleiswijk, The Netherlands. The female parent is a yellow *Phalaenopsis* pot plant named '21480-0002' (unpatented), while the male parent is a white striped *Phalaenopsis* pot plant named '21077-0001' (unpatented). A single plant was selected in July 2010 and has been asexually reproduced repeatedly by meristem tissue culture in Bleiswijk, The Netherlands over a 2.5-year period. The new variety has been found to retain its distinctive characteristics through successive asexual propagations.

Asexual reproduction of 'PHALFOLAK' by tissue culture was first performed in September 2012 in Bleiswijk, The Netherlands and has demonstrated that the new cultivar is firmly fixed and retained through successive generations of asexual reproduction.

Plant Breeder's Rights for this variety have been applied for in Europe on Sep. 29, 2014. 'PHALFOLAK' has not been made publicly available or sold anywhere in the world more than one year prior to the filing date of this application.

SUMMARY OF THE INVENTION

The following are the most outstanding and distinguishing characteristics of this new cultivar when grown under normal horticultural practices in Bleiswijk, The Netherlands.

1) Yellow striped flowers;
2) 1 to 3 peduncles;
3) Peduncle is short and sturdy;
4) The shape of the leaf is lanceolate and moderately elongated; and
5) Plants are propagated by meristem tissue culture.

DESCRIPTION OF THE PHOTOGRAPHS

This new *Phalaenopsis* plant is illustrated by the accompanying photographs which show the overall plant habit including blooms, buds and foliage of the plant; the colors shown are as true as can be reasonably obtained by conventional photographic procedures. The photographs are of a 50-week old plant grown in-a greenhouse in Bleiswijk, The Netherlands in January 2015.

DESCRIPTION OF THE NEW VARIETY

Figure 1:
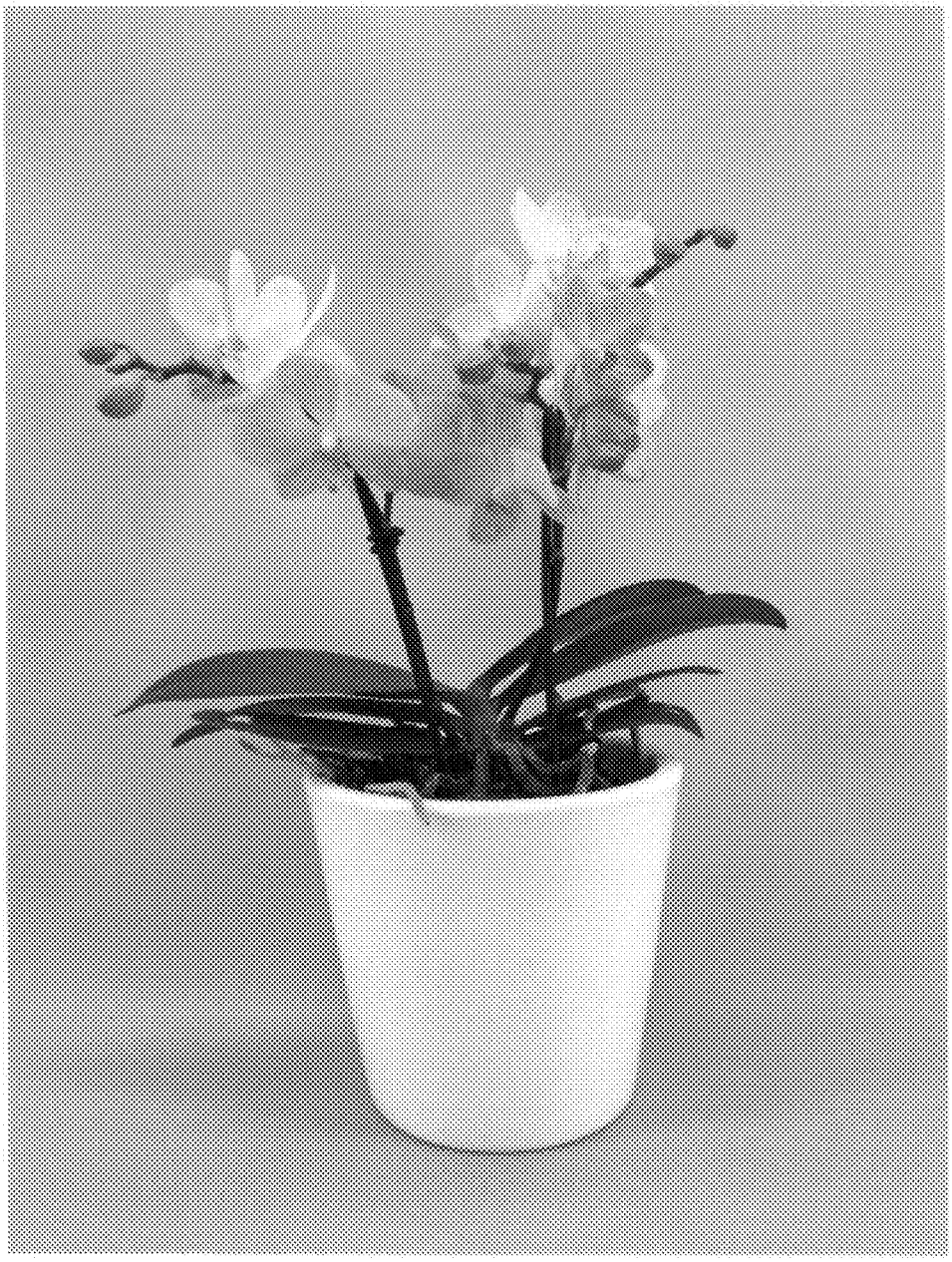
FIG. 1 shows the overall plant habit, including blooms, buds and foliage of 'PHALFOLAK'.
Figure 2:
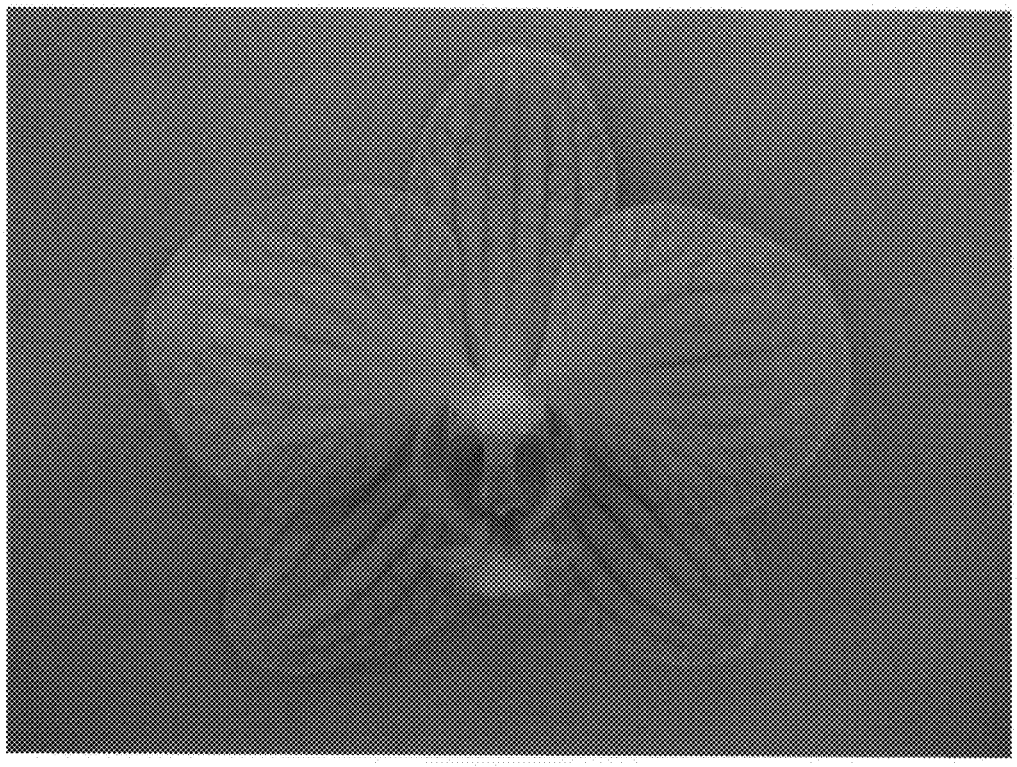
FIG. 2 shows a close-up of a flower of 'PHALFOLAK'.
Figure 3:
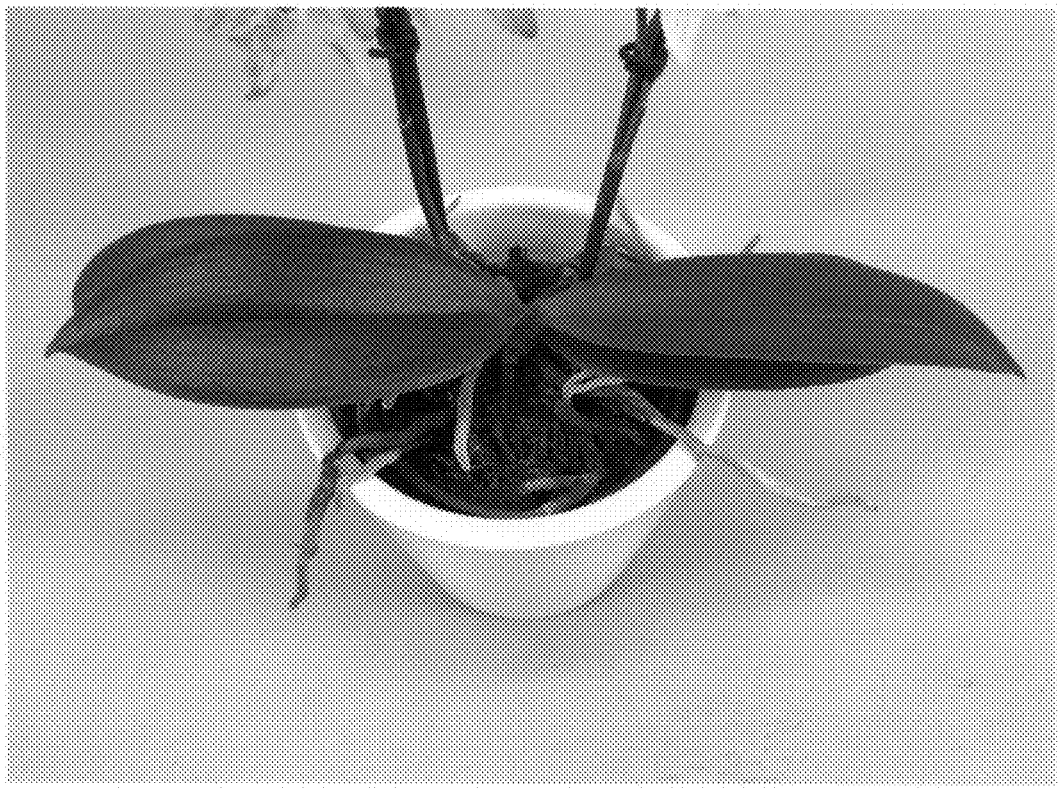
FIG. 3 shows a close-up of the leaves of 'PHALFOLAK'.

The following detailed description sets forth the distinctive characteristics of 'PHALFOLAK'. The data which define these characteristics were collected from asexual reproductions carried out in Bleiswijk, The Netherlands. The plant history was taken on 50-week old plants which were planted from a nursery tray in 12 centimeter pots and grown in a greenhouse between 27° C. to 29° C. for 30 weeks, continued by a cooling period of 8 weeks between 18° C. to 20° C. and 12 weeks in a greenhouse of 21° C. Observations were made in January 2015. Color readings were taken under 4000-6000 lux natural light in the greenhouse. Color references are primarily to The R.H.S. Colour Chart of The Royal Horticultural Society of London (R.H.S.) (2001).

DETAILED BOTANICAL DESCRIPTION

Classification:

*Family*.—Orchidaceae.

*Botanical*.—*Phalaenopsis* hybrid.

*Common name*.—*Phalaenopsis*.

*Variety name*.—'PHALFOLAK'.

Parentage:

*Female parent*.—*Phalaenopsis* cultivar '21480-0002' (unpatented).

*Male parent*.—*Phalaenopsis* cultivar '21077-0001' (unpatented).

Propagation:

*Type*.—Tissue culture.

Plant:

*Crop time* (*time to produce a finished flowering plant*).—48 to 50 weeks for a 12 cm pot.

*Growth habit of peduncle*.—Standard, green leaves, panicle.

*Height* (*including pot, including inflorescence*).—30.0 cm to 40.0 cm.

*Width* (*measured from leaf tips*).—24.0 cm to 29.0 cm.

*Vigor*.—Moderate.

Roots:

*Root description*.—Grey-green-colored roots with lightly branching lateral roots having grey-green colored root tips.

Leaves:

*Mature leaves*.—Quantity per plant: 7 to 9 leaves are produced before flowering. Length (fully expanded): 12.0 cm to 16.0 cm. Width: 5.0 cm to 6.0 cm. Shape: Lanceolate. Base shape: Moderately elongated. Apex: Unequal acute. Leaf blade angle with the petiole: Between 35 degrees and 50 degrees (measured from petiole to leaf). Leaf margin: Entire. Color: Upper surface: RHS 147A and towards the stem RHS 146A. Lower surface: RHS 146A. Texture: Rough. Thickness: 2.3 mm to 2.7 mm. Venation: Pattern: Parallel. Color of the midvein: Upper surface: RHS 147A. Lower surface: RHS 177A.

Peduncle:

*Quantity per plant*.—1 to 3.

*Number of flowers per peduncle*.—12 to 22.

*Length*.—22.0 cm to 27.0 cm.

*Diameter*.—3.9 mm to 4.2 mm.

*Strength*.—Sturdy.

*Aspect*.—Upright.

*Texture*.—Smooth.

*Color*.—Dark green (RHS 147A).

*Internode length*.—35.0 mm to 40.0 mm.

*Callosities*.—None.

Inflorescence description:

*Appearance*.—Upright to slightly pendant, panicle inflorescence with bilaterally symmetrical flowers that open in succession beginning with the lowermost flower.

*Inflorescence size*.—Height (from base to tip): 140.0 mm to 170.0 mm. Diameter: 3.5 mm to 3.8 mm.

*Flowering time*.—First flowers can be expected 10 to 11 months after planting in a 12 cm pot.

*Flower*.—Height: 55.0 mm to 60.0 mm. Diameter: 54.0 mm to 58.0 mm. Depth of lip: 12.0 mm to 15.0 mm.

*Flower longevity*.—On the plant: 7 to 11 weeks.

*Fragrance*.—Absent.

*Petals*.—Arrangement: Free. Shape: Semi-circular. Apex: Emarginated and slightly asymmetric. Margin: Entire. Length (from base to tip): 26.0 mm to 28.0 mm. Width: 23.0 mm to 25.0 mm. Color (when fully opened): Main color: Yellow (RHS 1C) striped (RHS 184B). At the base: Yellow (RHS 1C).

*Dorsal sepal*.—Shape: Elliptic. Margin: Entire. Length (from base to tip): 26.0 mm to 28.0 mm. Width: 15.0 mm to 17.0 mm. Color (when fully opened): Main color: Yellow (RHS 1C) striped (RHS 184B). At the base: Yellow (RHS 1C).

*Lateral sepals*.—Shape: Ovate. Margin: Entire. Length (from base to tip): 26.0 mm to 28.0 mm. Width: 16.0 mm to 18.0 mm. Color (when fully opened): Main color: Yellow (RHS 1C) striped (RHS 184B). At the base: Yellow (RHS 1C).

*Labellum* (*lip*).—Margin: Entire. Length: 15.0 mm to 17.0 mm. Width: 10.0 mm to 12.0 mm. Whiskers: Present. Length of whiskers: Short.

*Lateral lobe*.—Shape: Type IV (as described in the International Union for the Protection of New Varieties of Plants (UPOV) Test Guidelines for *Phalaenopsis*). Color: Yellow/purple (RHS 12A, 78B).

*Apical lobe*.—Shape: Elliptic. Color: Yellow (RHS 9B) red-purple towards the whiskers (RHS 60D).

*Callus*.—Color: Yellow (RHS 14A) dotted.

Reproductive organs:

*Arrangement*.—The stamens, style and stigmas are fused into a single, short structure called the column, possessing one terminal anther with pollen grains united into pollinia, which are covered by an anther cap. The stigma is located under the column behind the pollinia. The ovary is inferior with three carpels present.

*Column*.—Length: 7.5 mm to 9.5 mm. Diameter: 3.6 mm towards the top 4.5 mm. Color: White (RHS 115C) and light red-purple (RHS 74D).

*Pollinia*.—Quantity: 2. Size: 0.8 mm to 1.0 mm. Color: Yellow-orange (RHS 23A).

*Ovary*.—Length: 4.0 mm to 6.0 mm. Diameter: 1.8 mm to 2.0 mm.

*Pedicel*.—Length: 17.0 mm to 20.0 mm. Diameter: 2.3 mm to 2.5 mm.

Disease, pest, and stress resistance: No specific resistance or susceptibility observed.

Temperature tolerance: Tolerant to a low temperature of 15° C. and a high temperature about 30° C.

COMPARISON WITH PARENTAL AND COMMERCIAL VARIETIES

'PHALFOLAK' differs from female parent '21480-0002' (unpatented) in that 'PHALFOLAK' has yellow striped flowers, whereas '21480-0002' has yellow flowers.

'PHALFOLAK' differs from male parent '21077-0001' (unpatented) in that 'PHALFOLAK' has yellow striped flowers, whereas '21077-0001' has white striped flowers. Additionally, 'PHALFOLAK' has an elliptic apical lobe, whereas '21077-0001' has a triangular apical lobe.

'PHALFOLAK' differs from commercial variety 'PALCUWIM' (U.S. Plant Pat. No. 26,138) in that 'PHALFOLAK' has yellow striped flowers and striped lateral sepals, whereas 'PHALCUWIM' has flowers with a little light pink center and dotted lateral sepals. Additionally, 'PHALFOLAK' has a more narrow lip than 'PHALCUWIM'.

I claim:

1. A new and distinct variety of *Phalaenopsis* plant named 'PHALFOLAK', substantially as described and illustrated herein.

* * * * *